(12) United States Patent
Kourtakis et al.

(10) Patent No.: US 7,807,857 B2
(45) Date of Patent: Oct. 5, 2010

(54) LANTHANUM-PROMOTED SUPPORTED METAL CATALYSTS AND PROCESS FOR PRODUCING GUERBET ALCOHOLS USING SAME

(75) Inventors: Kostantinos Kourtakis, Media, PA (US); Ronnie Ozer, Arden, DE (US)

(73) Assignee: E. I. duPont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/642,974

(22) Filed: Dec. 21, 2009

(65) Prior Publication Data

US 2010/0160692 A1 Jun. 24, 2010

Related U.S. Application Data

(60) Provisional application No. 61/139,940, filed on Dec. 22, 2008.

(51) Int. Cl.
*C07C 29/34* (2006.01)
*C07C 29/36* (2006.01)

(52) U.S. Cl. .................. 568/902.2; 502/303; 502/102

(58) Field of Classification Search ............. 568/902.2; 502/303, 102
See application file for complete search history.

(56) References Cited

U.S. PATENT DOCUMENTS

| | | | |
|---|---|---|---|
| 3,972,952 | A | 8/1976 | Clark |
| 5,095,156 | A | 3/1992 | Radlowski et al. |
| 5,347,056 | A | 9/1994 | Watanabe et al. |
| 5,364,979 | A | 11/1994 | Radlowski et al. |
| 5,478,789 | A | 12/1995 | Hattori et al. |
| 2009/0054672 | A1 | 2/2009 | Kourtakis |
| 2009/0054703 | A1 | 2/2009 | Kourtakis |
| 2009/0054704 | A1 | 2/2009 | Kourtakis |
| 2009/0054705 | A1 | 2/2009 | Kourtakis |
| 2009/0054706 | A1 | 2/2009 | Kourtakis |
| 2009/0054707 | A1 | 2/2009 | Kourtakis |

FOREIGN PATENT DOCUMENTS

JP HEI 4-18042 1/1992

OTHER PUBLICATIONS

J. Logsdon in Kirk-Othmer Encyclopedia of Chemical Technology, John Wiley and Sons, Inc. NY (2001). (Book—Not available).
Michael N. Dvornikoff et al., "J. of Organic Chemistry", Condensation of Alcohols, vol. 11, pp. 540-542 (1957).
Charles N. Satterfield, "Hetergeneous Catalysis in Practice", McGraw-Hill, pp. 87-91 (1980).
Wateru Ueda et al., "J. Chem.Soc., Commun.", A Low-pressure Guerbet Reaction over Magnesium Oxide Catalyst, pp. 1558-1559 (1990).
Marcelo J. L. Gines, "J. of Catalysis," Bifunctional Condensation Reactions of Alcohols on Basic Oxides Modified by Copper and Potassium, vol. 176, pp. 155-172 (1998).
J. I. DiCosimo et al., "J. of Catalysis," Structure and Surface and Catalytic Properties of Mg-Al Basic Oxides, vol. 178, pp. 499-510 (1998).
J. I. DiCosimo et al., "J. of Catalysis," Structural Requirements and Reaction Pathways in Condensation Reactions of Alcohols on MgyAlOx Catalysts, vol. 190, pp. 261-275 (2000).
Takashi Tsuchida et al., "American Chemical Society," Direct Synthesis of n-Butanol from Ethanol over Nonstoichiometric Hydroxyapatite, pp. Est:8.1A-8.1l, (2006).

*Primary Examiner*—Elvis O Price

(57) ABSTRACT

The present invention relates to novel catalyst compositions and their use in a process for the catalytic conversion of ethanol to a reaction product comprising 1-butanol. The catalysts comprise Group II metal salts selected from the group consisting of oxides, carbonates, bicarbonates, hydroxides, and mixtures thereof, supported on a lanthanum-promoted oxide containing alumina.

14 Claims, No Drawings

LANTHANUM-PROMOTED SUPPORTED METAL CATALYSTS AND PROCESS FOR PRODUCING GUERBET ALCOHOLS USING SAME

CROSS-REFERENCE TO RELATED APPLICATIONS

This application claims benefit of priority from Provisional Application No. 61/139,940 filed Dec. 22, 2008. This application hereby incorporates by reference Provisional Application No. 61/139,940 in its entirety.

FIELD OF THE INVENTION

The present invention relates to novel catalyst compositions and their use in a process for the catalytic conversion of ethanol to a reaction product comprising 1-butanol. The catalysts comprise at least one Group II metal salt selected from the group consisting of oxides, carbonates, bicarbonates, hydroxides, and mixtures thereof, supported on a lanthanum-promoted oxide containing alumina. The promoted catalysts display good activity for conversion of ethanol to Guerbet alcohol products, including 1-butanol.

BACKGROUND

Efforts directed at improving air quality and increasing energy production from renewable resources have resulted in renewed interest in alternative fuels, such as ethanol and butanol, that might replace gasoline and diesel fuel, or be used as additives in gasoline and diesel fuel.

Methods for producing 1-butanol from ethanol are known. For example, 1-butanol can be prepared by condensation from ethanol over basic catalysts at high temperature using the so-called "Guerbet Reaction" (see for example, J. Logsdon in Kirk-Othmer Encyclopedia of Chemical Technology, John Wiley and Sons, Inc., New York, 2001).

M. N. Dvornikoff and M. W. Farrar, J. of Organic Chemistry (1957), 11, 540-542, disclose the use of MgO—$K_2CO_3$—$CuCrO_2$ catalyst system to promote ethanol condensation to higher alcohols, including 1-butanol. The disclosed liquid phase reaction using this catalyst showed a 13% conversion of ethanol and 47% selectivity to 1-butanol.

J. I. DiCosimo, et al., in Journal of Catalysis (2000), 190 (2), 261-275, describe the effect of composition and surface properties on alcohol-coupling reactions using $Mg_yAlO_x$ catalysts for alcohol reactions, including ethanol. Also condensation reactions on $Mg_yAlO_x$ samples involved the formation of products containing a new C—C bond, such as n-$C_4H_8O$ (or n-$C_4H_9OH$) and iso-$C_4H_8O$ (or iso-$C_4H_9OH$). They also describe, in Journal of Catalysis (1998), 178(2), 499-510, that the oxidation to acetaldehyde and the aldol condensation to n-butanol both involve initial surface ethoxide formation on a Lewis acid-strong base pair.

B. N. Dolgov et al., in Zhurnal Obshchei Khimii (1933), 3, 313-318, disclose production of BuOH by thermal decomposition of EtOH in the presence of $Fe_2O_3.Al_2O_3$ precipitated on carbon. Production of gaseous by-products was checked by activating the catalyst with the addition of La.

U.S. Pat. No. 5,478,789 discloses a hydrogenation reaction catalyst precursor comprising a catalyst carrier (A) and a metal oxide composition (B) carried on or mixed with the catalyst carrier (A). The catalyst carrier (A) comprises a carrier base material selected from a variety of materials, including alumina, and a coating of titanium oxide and/or titanium hydroxide. The metal oxide composition (B) comprises copper oxide, zinc oxide, and at least one oxide of a metal selected from the group consisting of an element of group IIa, an element of group IIIb, a lanthanide element, and an actinide element at specified weight ratios. Reduction of the catalyst precursor produces a hydrogenation reaction catalyst which can be used in a process for producing an alcohol by catalytically hydrogenating an organic carboxylic acid ester.

U.S. Pat. No. 5,347,056 discloses a process for producing α,β-unsaturated alcohol by selective hydrogenation of the aldehyde group in the unsaturated aldehyde starting material, using a catalyst which contains at least one oxide selected from the group consisting of oxides of yttrium, lanthanum, praseodymium, neodymium, and samarium, as a main active ingredient. The catalyst can contain, as a supplementary ingredient, a second element selected from a variety of listed metals, including calcium, strontium, and barium.

The production of Guerbet alcohols including 1-butanol has been described in the prior art. However, novel catalysts for making Guerbet alcohol products are still desired, especially those having improved activity and selectivity to desired products, which may provide economic advantages.

SUMMARY OF THE INVENTION

The present invention relates to novel catalyst compositions and their use in a process for the catalytic conversion of ethanol to a reaction product comprising 1-butanol. In one embodiment of the invention, a process is provided, the process comprising: contacting a reactant comprising ethanol with a catalyst composition at a temperature and pressure sufficient to produce said reaction product, wherein said catalyst composition comprises at least one Group II metal salt supported on a lanthanum-promoted oxide containing alumina and has the following empirical formula:

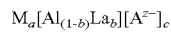

$$M_a[Al_{(1-b)}La_b][A^{z-}]_c$$

wherein:

(i) M is selected from the group consisting of $Mg^{2+}$, $Ca^{2+}$, $Sr^{2+}$, $Ba^{2+}$, $Ra^{2+}$, and combinations of these;

(ii) $A^{z-}$ is a monovalent or divalent anion selected from the group consisting of carbonate ($CO_3^{2-}$, wherein the charge, "z" is given by z=2), oxide ($O^{2-}$, wherein z=2), hydroxide ($OH^-$, wherein z=1), and bicarbonate ($HCO_3^-$, wherein z=1), or a mixture ($A^{z'-}_xA^{z''-}_y$) of these divalent and monovalent anions wherein $A^{z'-}$ and $A^{z''-}$ are different anions, with the caveat that when $A^{z-}$ is the mixture $A^{z'-}_xA^{z''-}_y$, the composite charge "z" is given by z=x(z')+y(z"), wherein x+y=1;

(iii) a is 0.01 to 0.4, including the endpoints of the range;

(iv) b is 0.0011 to 0.11, including the endpoints of the range; and (v) c=(2a/z)+[3(1−b)/z]+(3b/z).

In another embodiment of the invention, a catalyst composition is provided, the catalyst composition comprising: at least one Group II metal salt supported on a lanthanum-promoted oxide containing alumina and having the following empirical formula:

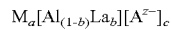

$$M_a[Al_{(1-b)}La_b][A^{z-}]_c$$

(i) M is selected from the group consisting of $Mg^{2+}$, $Ca^{2+}$, $Sr^{2+}$, $Ba^{2+}$, $Ra^{2+}$, and combinations of these;

(ii) $A^{z-}$ is a monovalent or divalent anion selected from the group consisting of carbonate ($CO_3^{2-}$, wherein the charge, "z" is given by z=2), oxide ($O^{2-}$, wherein z=2), hydroxide (OH⁻, wherein z=1), and bicarbonate (HCO$_3^-$, wherein z=1), or a mixture ($A^{z'-}_xA^{z''-}_y$) of these divalent and monovalent anions wherein $A^{z'-}$ and $A^{z''-}$ are different anions, with the caveat that when $A^{z-}$ is the mixture $A^{z'-}_xA^{z''-}_y$, the composite charge "z" is given by z=x(z')+y(z''), wherein x+y=1;

(iii) a is 0.01 to 0.4, including the endpoints of the range;

(iv) b is 0.0011 to 0.11, including the endpoints of the range; and (v) c=(2a/z)+[3(1−b)/z]+(3b/z).

DETAILED DESCRIPTION

The present invention relates to catalyst compositions which have improved activity and selectivity to Guerbet alcohol products, and a process for using such catalyst compositions to produce a reaction product comprising 1-butanol. Useful applications for the 1-butanol, which can be separated from the reaction product, include as an additive or blend component to diesel fuel. Ethanol is produced from renewable resources such as corn, sugar cane, or cellulosic feeds. In countries where ethanol production is operated at large scale such as Brazil, the ability to produce 1-butanol from ethanol offers an advantage.

The following definitions are used herein and should be referred to for interpretation of the claims and the specification.

The term "anhydrous ethanol" means ethanol containing less than about 0.1 weight percent water. As used herein, the term "dry ethanol" is used interchangeably with anhydrous ethanol. The term "EtOH" means ethanol.

The term "ethanol conversion" means the chemical reaction of ethanol to another compound.

The term "unreacted ethanol" means ethanol which has not been chemically reacted to another compound.

The term "BuOH" means 1-butanol.

The term "Guerbet alcohol products" means one or more alcohols produced by the Guerbet synthesis, wherein a primary or secondary alcohol having a methylene group at the α-position is condensed with itself, or with another alcohol also having a methylene group, to form a higher alcohol containing twice the number of carbon atoms of the single starting alcohol or, in the case of mixed alcohols, the sum of the number of carbon atoms in each reacting pair of alcohols. 1-Butanol is a Guerbet alcohol product of ethanol.

The term "base catalyst" means either a substance which has the ability to accept protons as defined by Brönsted, or a substance which has an unshared electron pair with which it can form a covalent bond with an atom, molecule or ion as defined by Lewis.

The term "wt %" means weight percent.

The term, "° C." means degrees Celsius.

The term "mg" means milligram(s).

The term "min" means minute(s).

The term "mL" means milliliter(s).

The term "M" means molar.

The term "o.d." means outer diameter.

The term "cc" means cubic centimeter(s).

The term "cm" means centimeter.

The term "temp" means temperature.

The term "MPa" means mega Pascal.

The term "GC/MS" means gas chromatography/mass spectrometry.

General Methods and Materials

The catalyst compositions useful in the present invention comprise at least one Group II metal salt selected from the group consisting of oxides, carbonates, bicarbonates, hydroxides, and/or mixtures thereof, supported on a lanthanum-promoted oxide containing alumina. In one embodiment, the catalyst compositions have the following empirical formula: $M_a[Al_{(1-b)}La_b][A^{z-}]_c$.

In the empirical formula provided herein "M" is a metal selected from the group consisting of $Mg^{2+}$, $Ca^{2+}$, $Sr^{2+}$, $Ba^{2+}$, $Ra^{2+}$, and combinations thereof; "$A^{z-}$" is a monovalent or divalent anion, and "z" is the charge of the anion.

The anion $A^{z-}$ can be at least one monovalent or divalent anion or anion radical selected from the group consisting of carbonate (that is, $CO_3^{2-}$, wherein the charge, "z" is given by z=2), oxide (that is, $O^{2-}$, wherein z=2), hydroxide (that is, OH⁻, wherein z=1), and bicarbonate (that is, $HCO_3^-$, wherein z=1), or a mixture ($A^{z'-}_xA^{z''-}_y$) of these divalent and monovalent anions. One of ordinary skill will understand that when z=1, the "1" is understood and need not be printed in the formula.

When "$A^{z-}$" represents a mixture of anions or anion radicals, the empirical formula can be represented by: $M_a[Al_{(1-b)}La_b][A^{z'-}_xA^{z''-}_y]$, with the caveat that "$A^{z'-}$" and "$A^{z''-}$" are different anions, and when $A^{z-}$ is the mixture $A^{z'-}_xA^{z''-}_y$, the composite anionic charge "z" is given by z=x(z')+y(z''), and x+y=1;

In one embodiment, "M" is $Ca^{2+}$, $Sr^{2+}$, or $Ba^{2+}$, and "$A^{z-}$" is carbonate, oxide, or a mixture of these; a is 0.05 to 0.2, and b is 0.005 to 0.05.

The at least one Group II metal salt is supported on a lanthanum-promoted oxide containing alumina, for example gamma alumina (γ-alumina) or eta (η-alumina), or other alumina phase which is stable at the temperatures used for catalyst calcination and conversion of ethanol to a reaction product comprising 1-butanol. γ-Alumina is preferred for its characteristic high surface area. It is well known that aluminas are generally prepared by dehydration of various aluminum hydroxides, and that the particular crystalline form that is obtained depends on the temperature and reaction time history of the hydroxides. See, for example, Charles N. Satterfield, (*Heterogeneous Catalysis in Practice*, (1980) McGraw-Hill, pp. 87-91).

The catalyst compositions of the invention can be synthesized by the following method. A support containing γ-alumina is impregnated with a lanthanum salt or precursor, such as lanthanum nitrate or acetate, by techniques known in the art. For example, a slurry of a lanthanum salt or precursor and γ-alumina can be prepared, then spray-dried. Following the spray-drying step, the support can be heated to a temperature sufficient to decompose the lanthanum salt or precursor to a catalytically active species. For lanthanum nitrates or acetates, this temperature is typically greater than about 650° C. to generate a catalyst comprising a metal oxide or a carbonate. Alternatively, a lanthanum salt or precursor can be introduced to the γ-alumina by forming a solution of the lanthanum salt or precursor and subsequently contacting that solution with the γ-alumina support by incipient wetness, so that the pore volume of the support is not exceeded by the volume of the liquid added. Multiple impregnation and drying cycles can be used to achieve the final desired stoichiometry.

Following the formation of the lanthanum-promoted γ-alumina support, the Group II metal salt or precursor can be added by similar techniques. The corresponding metal salt or precursor can be dissolved in an appropriate solvent and added to the lanthanum-promoted alumina support using the same techniques described above.

Alternatively, the lanthanum and Group II metal salts or precursors can be added concurrently via a plurality of individual metal salt solutions to the support, or the Group II metal salt can be added to the support first, followed by the lanthanum salt or precursor.

The catalyst compositions useful in the process of the invention can be prepared as described above. The catalyst compositions may be used in the form of powders, granules, or other particulate forms. Selection of an optimal average particle size for the catalyst composition will depend upon such process parameters as reactor residence time and desired reactor flow rates.

In the process for making a reaction product comprising 1-butanol, a stream of gas phase ethanol is contacted with at least one catalyst composition comprising at least one Group II metal salt, wherein the salt is selected from the group consisting of oxides, carbonates, bicarbonates, hydroxides, and mixtures thereof, supported on a lanthanum-promoted oxide containing alumina at a temperature and pressure sufficient to produce a reaction product comprising 1-butanol. The ethanol stream may be diluted with an inert gas, for example nitrogen, argon, carbon dioxide, or a combination of these. Suitable temperatures can be in the range of about 150° C. to about 500° C., for example about 200° C. to about 500° C. Suitable pressures are from about 0.1 mPa to about 20.7 MPa. The reaction product can further comprise water, unreacted ethanol (if less than complete ethanol conversion occurs), other butanol isomers, higher alcohols, and other organic species. The butanol is predominantly 1-butanol.

The catalytic conversion of ethanol to the reaction product comprising 1-butanol can be run in either batch or continuous mode as described, for example, in H. Scott Fogler, (*Elements of Chemical Reaction Engineering*, $2^{nd}$ Edition, (1992) Prentice-Hall Inc, CA). Suitable reactors include fixed-bed, adiabatic, fluid-bed, transport bed, and moving bed.

During the course of the reaction, the catalyst may become fouled, and therefore it may be necessary to regenerate the catalyst. Preferred methods of catalyst regeneration include, contacting the catalyst with a gas such as, but not limited to, air, steam, hydrogen, nitrogen or combinations thereof, at an elevated temperature, although care must be taken not to use a temperature that is so high that the regeneration results in a loss of surface area or other unwanted effects. If catalyst regeneration is desired, the catalyst may be regenerated in situ in the reactor or ex situ and then introduced into the reactor.

One skilled in the art will know that conditions, such as temperature, catalytic metal, catalyst support, reactor configuration and time can affect the reaction kinetics, product yield and product selectivity. Standard experimentation can be used to optimize the yield of 1-butanol from the reaction.

1-Butanol can be separated from the reaction product by known chemical engineering methods, including distillation. Other specific chemicals (or combinations of chemicals) also can be removed from the reaction product using known chemical engineering methods. The specific methods will be dependent on the nature of the reaction product, which, in turn, is dependent on the specific catalyst composition used and the reaction conditions, particularly the extent of ethanol conversion.

EXAMPLES

Barium nitrate was obtained from Aldrich Chemical Company, strontium acetate from Alfa Aesar, calcium acetate from EM Sciences, barium acetate from JT Baker, γ-alumina support from Engelhard Corporation. Lanthanum-promoted γ-alumina catalyst support AL2301 was obtained from Davison Chemical. This material contains 4 weight percent $La_2O_3$ and 96 weight percent γ-$Al_2O_3$. Ethanol (200 proof) was obtained from Sigma-Aldrich (St. Louis, Mo.) contained less than 0.200 weight percent water.

Example 1

Ba Compound on Lanthanum-Promoted γ-Alumina

Barium catalyst composition having empirical formula $Ba_a[Al_{(1-b)}La_b][A^{z-}]_c$ where $A^{z-}$ is $CO_3^{2-}$ or $O^{2-}$ or a mixture of these; a=0.14; b=0.013; and c=1.64.

Catalyst Composition Preparation:

14.40 g of barium nitrate (molecular weight 269.18 g/mole) was dissolved in 20 g of water. This solution was added dropwise to 20 g of Davison Catalyst AL2301 support (containing 3 wt % La) to imbibe the material on the support. The support was prepared by Davison by spray-drying a slurry containing a soluble lanthanum salt with pre-formed γ-alumina support. The impregnated material was dried in air for 16 hours.

The powder was placed into a zirconia boat then calcined in a tube furnace in flowing air. The internal diameter of the tube furnace was 10 cm and a volumetric airflow of 1.7 liters/minute (corresponding to 20 cm/min linear velocity) was used. The calcination protocol involved heating to 120° C. and holding at that temperature for 4 hours, followed by heating at a rate 3.8 minutes/minute to 500° C. The material was soaked at 500° C. for 6 hours in the flowing air before cooling the furnace to room temperature. The product was lightly ground, and pressed into small pellets. It was subsequently granulated and screened through −20, +40 mesh sieves for a microreactor evaluation as described below.

Example 2

Sr Compound on Lanthanum-Promoted γ-Alumina

Strontium catalyst composition having empirical formula $Sr_a[Al_{(1-b)}La_b][A^{z-}]_c$ where $A^{z-}$ is $CO_3^{2-}$ or $O^{2-}$ or a mixture of these; a=0.14; b=0.013; and c=1.64.

Catalyst Composition Preparation:

The same procedure as described in Example 1 was used, with the following exceptions: 11.97 g of strontium acetate (molecular weight 223.71 g/mole) was used instead of barium nitrate. The catalyst composition was evaluated as described below.

Example 3

Ca Compound on Lanthanum-Promoted γ-Alumina

Calcium catalyst composition having empirical formula $Ca_a[Al_{(1-b)}La_b][A^{z-}]_c$ where $A^{z-}$ is $CO_3^{2-}$ or $O^{2-}$ or a mixture of these; a=0.13; b=0.013; and c=1.63.

Catalyst Composition Preparation:

The same procedure as described in Example 1 was used, with the following exceptions: 8.81 g of calcium acetate (molecular weight 176.18 g/mole) was used instead of barium nitrate. The catalyst composition was evaluated as described below.

Comparative Example A 29.1 wt % BaO (Nominally) on γ-Alumina

Barium catalyst composition without lanthanum promoter and having empirical formula $Ba_a[Al_{1.04}][A^{z-}]_c$ where $A^{z-}$ is $CO_3^{2-}$ or $O^{2-}$ or a mixture of these; a=0.14; and c=1.7.

Catalyst Composition Preparation:

The same procedure as described in Example 1 was used, with the following exceptions: 13.66 g of barium acetate (molecular weight 255.42 g/mole) was used instead of barium nitrate, and 20 g of γ-alumina support (Engelhard Corporation) was used instead of the Davison Al2301 catalyst support. The catalyst composition was evaluated as described below.

Comparative Example B 21.7 wt % SrO (Nominally) on γ-Alumina

Strontium catalyst composition without lanthanum promoter and having empirical formula $Sr_a[Al_{1.04}][A^{z-}]_c$ where $A^{z-}$ is $CO_3^{2-}$ or $O^{2-}$ or a mixture of these; a=0.13; and c=1.69

Catalyst Composition Preparation:

The same procedure as described in Example 1 was used, with the following exceptions: 11.00 g of strontium acetate was used instead of barium nitrate, and 20 g of y-alumina support was used instead of the Davison Al2301 catalyst support. The catalyst composition was evaluated as described below.

Comparative Example C 12.9 wt % CaO (Nominally) on γ-Alumina

Calcium catalyst composition without lanthanum promoter and having empirical formula $Ca_a[Al_{1.04}][A^{z-}]_c$ where $A^{z-}$ is $CO_3^{2-}$ or $O^{2-}$ or a mixture of these; a=0.14; and c=1.70.

Catalyst Composition Preparation:

The same procedure as described in Example 1 was used, with the following exceptions: 9.338 g of calcium acetate was used instead of barium nitrate, and 20 g of γ-alumina support was used instead of the Davison Al2301 catalyst support.

Reactor Evaluations of Catalyst Compositions by Conversion of Ethanol to a Reaction Product Containing 1-Butanol Each catalyst composition was evaluated using the following procedure. Approximately 2 cc of catalyst composition was loaded on a stainless steel mesh support within a 18"×½" (45.7 cm×1.3 cm) outside diameter (o.d.) type 316 stainless steel tube reactor with inlets for gas and liquid feeds. The catalyst composition was then pre-conditioned in situ in the reactor by flowing nitrogen gas, initially at room temperature, raising the temperature to 350° C., holding it there for one hour, lowering the temperature to 180° C., flowing hydrogen gas at 15 cc/hr for one hour, reintroducing nitrogen gas at a flow rate of 15 ml/min, and increasing the reactor temperature to that shown in Table 1 to introduce the ethanol to generate reaction data. At reaction temperature nitrogen flow was set at 15 ml/min and ethanol flow at 1.03 ml/hr. The majority of the reaction off-gases were condensed throughout a 60 minute reaction time in cold N-methylpyrrolidone solvent, and the resultant solution was analyzed using an Agilent™ 5890 GC equipped with flame ionization and mass selective detectors. Alternatively the gaseous product stream was kept at 200° C. and fed directly to an Agilent™ 6890 GC equipped with flame ionization and mass selective detectors. Results are shown in Table 1 below, wherein "EtOH" means ethanol, "BuOH" means 1-butanol, "Conv." means conversion, and "Sel." means selectivity. Ethanol conversion (%) was calculated as follows: [(1−carbon moles of unreacted ethanol)/carbon moles of total outlet gases]times 100. Selectivity (%) was calculated as follows: (carbon moles of product/carbon moles of ethanol reacted) times 100. For selectivity to total alcohols the above selectivity calculation was used, except that total carbon moles of alcohol products was used (including butanol) as "product". Other products observed included aldehydes such as acetaldehyde and butanal, aromatics such as xylene, and ketones such as heptanone.

TABLE 1

Results from Catalyst Evaluations.

| Example # | Temperature (° C.) | EtOH Conversion | 1-BuOH Selectivity | Total Alcohol Selectivity |
|---|---|---|---|---|
| 1 | 400 | 38 | 23 | 43 |
| 2 | 400 | 29 | 34 | 52 |
| 3 | 400 | 30 | 35 | 48 |
| Comparative Example A | 400 | 29 | 29 | 32 |
| Comparative Example B | 400 | 29 | 16 | 29 |
| Comparative Example C | 400 | 15 | 38 | 39 |

The results show that the lanthanum-promoted, supported metal catalyst compositions of the invention displayed good activity for conversion of ethanol to Guerbet alcohol products, including 1-butanol, and improved selectivity to total alcohols when compared to the unpromoted catalysts of the Comparative Examples.

Although particular embodiments of the present invention have been described in the foregoing description, it will be understood by those skilled in the art that the invention is capable of numerous modifications, substitutions, and rearrangements without departing from the spirit or essential attributes of the invention. Reference should be made to the appended claims, rather than to the foregoing specification, as indicating the scope of the invention.

What is claimed is:

1. A process for making a reaction product comprising 1-butanol, comprising the step:

contacting a reactant comprising ethanol with a catalyst composition at a reaction temperature and pressure sufficient to produce said reaction product, wherein said catalyst composition comprises at least one Group II metal salt supported on a lanthanum-promoted oxide containing alumina and has the following empirical formula:

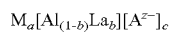

$$M_a[Al_{(1-b)}La_b][A^{z-}]_c$$

wherein:

(i) M is selected from the group consisting of $Mg^{2+}$, $Ca^{2+}$, $Sr^{2+}$, $Ba^{2+}$, $Ra^{2+}$, and combinations of these;

(ii) $A^{z-}$ is a monovalent or divalent anion selected from the group consisting of carbonate ($CO_3^{2-}$, wherein the charge, "z" is given by z=2), oxide ($O^{2-}$, wherein z=2), hydroxide ($OH^-$, wherein z=1), and bicarbonate ($HCO_3^-$, wherein z=1), or a mixture ($A^{z'-}_{x}A^{z''-}_{y}$) of these divalent and monovalent anions wherein $A^{z'-}$ and $A^{z''-}$ are different anions, with the caveat that when $A^{z-}$ is the mixture $A^{z'-}_{x}A^{z''-}_{y}$, the composite charge "z" is given by z=x(z')+y(z''), wherein x+y=1;

(iii) a is 0.01 to 0.4, including the endpoints of the range;
(iv) b is 0.0011 to 0.11, including the endpoints of the range; and
(v) c=(2a/z)+[3(1−b)/z]+(3b/z).

2. The process of claim 1, wherein the temperature is from about 200° C. to about 500° C.

3. The process of claim 1, wherein the pressure is from about 0.1 mPa to about 20.7 MPa.

4. The process of claim 1, wherein M is $Ca^{2+}$, $Ba^{2+}$, or $Sr^{2+}$; $A^{z-}$ is $CO_3^{2-}$ or $O^{2-}$ or a mixture of these; a is 0.05 to 0.2; b is 0.005 to 0.05.

5. The process of claim 1, wherein M is $Ca^{2+}$.

6. The process of claim 1, wherein M is $Sr^{2+}$.

7. The process of claim 1, wherein M is $Ba^{2+}$.

8. The process of claim 1, wherein the alumina is γ-alumina.

9. A catalyst composition comprising:
at least one Group II metal salt supported on a lanthanum-promoted oxide containing alumina and having the following empirical formula:

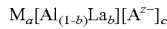

$M_a[Al_{(1-b)}La_b][A^{z-}]_c$ wherein:
(i) M is selected from the group consisting of $Mg^{2+}$, $Ca^{2+}$, $Sr^{2+}$, $Ba^{2+}$, $Ra^{2+}$, and combinations of these;
(ii) $A^{z-}$ is a monovalent or divalent anion selected from the group consisting of carbonate ($CO_3^{2-}$, wherein the charge, "z" is given by z=2), oxide ($O^{2-}$, wherein z=2), hydroxide ($OH^-$, wherein z=1), and bicarbonate ($HCO_3^-$, wherein z=1), or a mixture ($A^{z'-}_{x}A^{z''-}_{y}$) of these divalent and monovalent anions wherein $A^{z'-}$ and $A^{z''-}$ are different anions, with the caveat that when $A^{z-}$ is the mixture $A^{z'-}_{x}A^{z''-}_{y}$, the composite charge "z" is given by z=x(z')+y(z''), wherein x+y=1;
(iii) a is 0.01 to 0.4, including the endpoints of the range;
(iv) b is 0.0011 to 0.11, including the endpoints of the range; and
(v) c=(2a/z)+[3(1−b)/z]+(3b/z).

10. The composition of claim 9, wherein M is $Ca^{2+}$, $Sr^{2+}$, or $Ba^{2+}$; $A^{z-}$ is $CO_3^{2-}$ or $O^{2-}$ or a mixture of these; a is 0.05 to 0.2; b is 0.005 to 0.05.

11. The catalyst composition of claim 9, wherein M is $Ca^{2+}$.

12. The catalyst composition of claim 9, wherein M is $Sr^{2+}$.

13. The catalyst composition of claim 9, wherein M is $Ba^{2+}$.

14. The catalyst composition of claim 9, wherein the alumina is γ-alumina.

* * * * *